United States Patent [19]

Oxman et al.

[11] Patent Number: 5,415,544

[45] Date of Patent: May 16, 1995

[54] PRELOADED THERMOPLASTIC DENTAL IMPRESSION TRAY

[75] Inventors: Joel D. Oxman, Minneapolis; F. Andrew Ubel, III, St. Paul; Lani S. Kangas, Woodbury; Todd R. Williams, Lake Elmo, all of Minn.

[73] Assignee: Minnesota Mining and Manufacturing Company, St. Paul, Minn.

[21] Appl. No.: 916,862

[22] PCT Filed: Feb. 25, 1991

[86] PCT No.: PCT/US91/01245

§ 371 Date: Aug. 6, 1992

§ 102(e) Date: Aug. 6, 1992

[87] PCT Pub. No.: WO91/12776

PCT Pub. Date: Sep. 5, 1991

[51] Int. Cl.$^6$ .............................................. A61C 9/00
[52] U.S. Cl. ...................................... 433/48; 433/214
[58] Field of Search .......................... 433/37, 48, 214; 128/861, 862

[56] References Cited

U.S. PATENT DOCUMENTS

| | | | |
|---|---|---|---|
| 2,705,492 | 4/1955 | Chandler | 128/862 |
| 3,124,129 | 3/1964 | Grossberg | 128/862 |
| 3,333,582 | 8/1967 | Cathcart | 128/862 |
| 3,382,202 | 5/1968 | Forrester et al. | 260/32.6 |
| 3,427,161 | 2/1969 | Laridon et al. | 96/35.1 |
| 3,756,827 | 9/1973 | Chang et al. | 96/86 |
| 3,759,807 | 9/1973 | Osborn et al. | 204/159.23 |
| 3,767,627 | 10/1973 | Schoen | 260/78.3 |
| 3,923,729 | 12/1975 | Clendinning et al. | 260/40 |
| 4,059,715 | 11/1977 | Pletcher | 428/349 |
| 4,071,424 | 1/1978 | Dart et al. | 204/159.15 |
| 4,182,829 | 1/1980 | Walkowiak et al. | 528/75 |
| 4,227,877 | 10/1980 | Tureaud et al. | 433/37 |
| 4,240,415 | 12/1980 | Wartman | 128/90 |
| 4,327,013 | 4/1982 | Peters | 524/538 |
| 4,361,528 | 11/1982 | Ginsburg et al. | 264/168 |
| 4,445,854 | 5/1984 | Bekey et al. | 433/37 |
| 4,483,333 | 11/1984 | Wartman | 128/90 |
| 4,552,906 | 11/1985 | Podszun et al. | 523/115 |
| 4,569,342 | 2/1986 | von Nostitz | 128/136 |
| 4,642,126 | 2/1987 | Zador et al. | 51/295 |

(List continued on next page.)

FOREIGN PATENT DOCUMENTS

| | | |
|---|---|---|
| 0096020 | 12/1983 | European Pat. Off. . |
| 0173085 | 7/1984 | European Pat. Off. . |
| 150952 | 8/1985 | European Pat. Off. . |
| 2078675 | 11/1971 | France . |
| 3810907 | 10/1988 | Germany . |
| 63-171554 | 1/1987 | Japan . |
| 63-270759 | 11/1988 | Japan . |
| 1304112 | 1/1973 | United Kingdom . |
| 83/02898 | 9/1983 | WIPO . |
| WO-9014052 | 11/1990 | WIPO . |

OTHER PUBLICATIONS

Tone$^R$ P-300 and P-700 High Molecular Weight Caprolactone Polymers (1988 product literature of Union Carbide Corp.).

Chem. Abs. 95:225704U.

Aqueron TM bite registration sticks and custom tray material (cover letter dated 8 Dec. 1989 from E. M. Natt Ltd. with brochure form Erkodent Company.

Patent Abstract of Japanese Publication No. JP-A-12 69 613, published Oct. 26, 1989.

Primary Examiner—Cary E. O'Connor
Attorney, Agent, or Firm—Gary L. Griswold; Walter N. Kirn; Dale A. Bjorkman

[57] ABSTRACT

A preloaded impression tray (5a), comprising a thermoplastic impression material (7) at least partially enveloped by a shell (1a), the thermoplastic impression material being a plasticized solid and having:

(i) a softening point that comfortably can be withstood by oral tissues, (ii) sufficient depth in the shell and fluidity when softened to conform accurately to adult dentition and the gingival margin, and (iii) sufficient strength and flexibility when resolidified in the mouth to permit removal of the impression material from teeth without tearing or undesirable distortion.

13 Claims, 1 Drawing Sheet

U.S. PATENT DOCUMENTS

| | | | |
|---|---|---|---|
| 4,659,786 | 4/1987 | Kawakami et al. | 525/415 |
| 4,740,245 | 4/1988 | Futami et al. | 106/35 |
| 4,761,136 | 8/1988 | Madhaven et al. | 522/90 |
| 4,768,951 | 9/1988 | Abiru et al. | 433/48 |
| 4,776,792 | 10/1988 | Wagner et al. | 433/71 |
| 4,828,583 | 5/1989 | Oxman et al. | 51/295 |
| 4,835,203 | 5/1989 | Sieverding | 524/277 |
| 4,859,742 | 8/1989 | Pattein et al. | 525/131 |
| 4,867,680 | 9/1989 | Hare et al. | 433/37 |
| 4,912,174 | 3/1990 | Grouiller | 525/415 |
| 5,011,407 | 4/1991 | Pelerin | 433/48 |
| 5,028,667 | 7/1991 | McLain et al. | 525/415 |
| 5,066,231 | 11/1991 | Oxman et al. | 433/48 |

PRELOADED THERMOPLASTIC DENTAL IMPRESSION TRAY

CROSS-REFERENCE TO RELATED APPLICATION

This application is a continuation-in-part of U.S. patent application Ser. No. 07/484,695, filed Feb. 23, 1990.

FIELD OF THE INVENTION

This invention relates to thermoplastic molding compositions. It also relates to dental impression-taking, to the manufacture of dentures, crowns, bridges and other oral prosthetic devices, and to general-purpose model-making.

BACKGROUND OF THE INVENTION

High molecular weight poly (epsilon-caprolactone) (also known as "polycaprolactone"), various thermoplastic acrylics, and other heat-softenable materials have been used to take impressions of teeth or to make custom dental trays. References describing such thermoplastic compositions include U.S. Pat. Nos. 2,020,311, 4,227,877, 4,361,528, 4,401,616, 4,413,979, 4,569,342, 4,619,610 4,657,509, 4,659,786, 4,768,951, 4,776,792, and 4,835,203. Other references include Kokai (Japanese Published Pat. Appl.) Nos. Sho 63[1988]-96536 [which discloses oil-extended ethylene vinyl acetate ("EVA") copolymers that are stored in syringes before use]; Sho 63[1988]-171554 and Sho 63[1988]-270759; and TONE® POLYMERS P-300 AND P-700 High Molecular Weight Caprolactone Polymers (1988 product literature of Union Carbide Corp.). In the main, the thermoplastic materials of these references are used without a surrounding shell, or their manner of use is not specifically described. In some instances the thermoplastic materials are themselves shaped to form a custom tray which is in turn used as a shell surrounding a conventional non-thermoplastic elastomeric impression material such as a polysiloxane. The thermoplastic materials of the '610 and '792 patents are exceptions; both employ a thin thermoplastic sheet surrounded by a rigid tray. In each of these latter two patents (and in the "OCCLUSAL HARMONY" dental tray from Advantage Dental Products, Inc., a commercial version of the tray shown in the '792 patent) the thin thermoplastic sheet is used to make a bite registration of only the occlusal tooth surfaces.

Other commercially available dental impression trays that contain a heat-softenable thermoplastic include the "EASY TRAY" from Oral Dynamics Inc. Division of Anson International, the "HEAT FORM" tray from Shofu, Inc., and the "AQUERON" custom tray from Erkodent Company. These latter three products are heated and shaped to conform to the shape of a patient's dental tissue, then typically filled with elastomeric impression material and reinserted in the patient's mouth to take an impression of the dental tissue.

There are only a few preloaded impression trays (trays intended to be sold with the impression material in the tray) described in the dental literature. U.S. Pat. Nos. 4,553,936 and 4,867,680 describe preloaded trays containing light-curable acrylic impression materials. The impression materials are not said to be thermoplastic. Instead, they apparently are flowable or pourable at room temperature, and are held in the tray using a flexible cover sheet or skin material.

Kokai Hei 2[1990]-45049 describes an impression technique that employs a thermoplastic propionic cellulose acetate impression material that is heated in a rod shape, bent to conform to an arch-shaped tray, "piled" on the tray, and inserted into a patient's mouth while still warm. The tray is not a preloaded dental impression tray, in that the impression material resides in the tray for only a short time before it is inserted in a patient's mouth, and is not intended to be sold in preloaded form.

OTHER REFERENCES

Kokai Nos. Hei 2[1990]-60642 and Hei 2[1990]-60672 were not published until 1 Mar. 1990. They refer respectively to a custom impression tray and a mouthguard, both being made of heat-softenable thermoplastic resin.

European Pat. Application No. 0 359 135 was not published until 21 Mar. 1990. It describes a mouthpiece (a mouthguard) for use in contact sports. The mouthpiece is made of inner and outer layers of thermoplastic EVA resins. The outer layer is required to be impact resistant so that it will survive strong impacts. The outer layer is also said to have a melting point preferably above 60° C., more preferably from 63° to 68° C. If made of EVA, the outer layer is required to have a melt flow rate ("MFR") less than 65 g/10 min. The mouthpiece is formed by heating it to a temperature that will melt the inner layer but not the outer layer. This reference does not disclose or suggest dental impressioning to make a dental model.

U.S. Pat. No. 4,654,006 describes thermoplastic polyolefin elastomers for custom-fitted denture bases.

SUMMARY OF THE INVENTION

Currently-used dental impression techniques often require several time-consuming steps, and frequently employ expensive two-part curable materials such as polyvinylsiloxanes and polyethers. Despite their cost, these expensive impression materials are preferred by many clinicians owing to factors such as accuracy, elasticity (and the consequent ease of removal from undercuts such as are commonly found in adult dentition), and good detail reproduction. However, a need remains for new impression materials and techniques that yield high-quality dental impressions with improved speed and ease of use but lower potential cost. The present invention handily addresses that need.

The invention includes a method for preparing a dental model using a preloaded impression tray, comprising the steps of:

(a) heating a thermoplastic impression material in the tray until the material melts or softens, the material being a solid at 38° C. and having:
  (i) a softening point that comfortably can be withstood by oral tissues,
  (ii) sufficient depth in the tray and fluidity when softened to conform accurately to adult dentition and the gingival margin, and
  (iii) sufficient flexibility when resolidified in the mouth to permit removal of the impression material from teeth without tearing or undesirable distortion; and, after a dental impression has been taken using the tray;

(b) pouring a modeling compound into the impression to form a dental model.

The invention also includes a preloaded impression tray comprising a thermoplastic impression material at least partially enveloped by a shell, the thermoplastic impression material being a plasticized solid and having:

(i) a softening point that comfortably can be withstood by oral tissues, (ii) sufficient depth in the shell and fluidity when softened to conform accurately to adult dentition and the gingival margin, and (iii) sufficient strength and flexibility when resolidified in the mouth to permit removal of the impression material from teeth without tearing or undesirable distortion.

A preferred preloaded tray is customizable and has a heat-softenable thermoplastic shell that melts or softens at a temperature less than 60° C. A second preferred preloaded tray is noncustomizable and has a substantially rigid metal or plastic shell that will not melt below 75° C.

DETAILED DESCRIPTION

Figure 1:
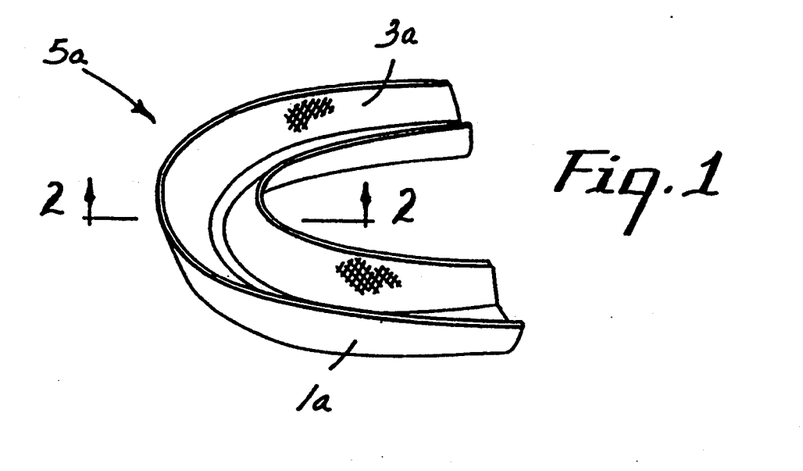
FIG. 1 is a perspective view of a shell for a tray of the invention.
Figure 2:
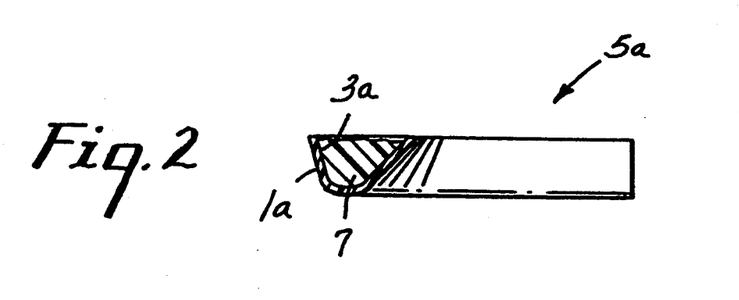
FIG. 2 is a section through line 2—2 of FIG. 1, showing a tray of the invention including its thermoplastic impression material.

Referring to the Drawing, FIGS. 1 and 2 show an arch-shaped tray 5a having a shell 1a of thermoplastic material that will soften if heated in a 60° C. water bath (not shown). The warmed tray can be custom-shaped in the mouth to account for variations in patient dentition. Accordingly, the dentist need keep on hand only a few tray sizes rather than a large assortment of trays. Also, by imparting a custom shape to the tray, an accurate impression having a desirably thin layer of solidified impression material will be obtained. Shell 1a is lined with an optional woven scrim 3a, which assists in formation of a firm bond between shell 1a and thermoplastic impression material 7 after the impression material resolidifies. Thermoplastic impression material 7 has certain important properties described in more detail below. Tray 5a can be sold to an end-user with thermoplastic impression material 7 preloaded in the tray prior to shipment. The preloaded tray can be packaged and subjected to routine warehouse handling and shipment without damage. Preferably the tray is stored at less that 60° C. (e.g., at room temperature) before use.

The tray can also have a shell (not shown) of rigid metal or plastic. The rigid shell does not melt below 75° C., and thus is not custom-shaped in the mouth. Accordingly, a larger inventory of tray shapes and sizes will typically be required. However, trays with rigid shells will be preferred by many practitioners, especially for applications such as "double bite" trays and partial arch (e.g., quadrant) trays.

The invention provides a simplified dental impression system. Traditional impressioning systems employ one or more low viscosity, flowable elastomeric materials such as an alginate, hydrocolloid, polyvinylsiloxane, polyether, or polysulfide contained in a fairly rigid adhesive-coated plastic or metal arch-shaped shell. The elastomeric material often is applied both to the dental tissue to be modeled and to the shell. The elastomeric material and surrounding shell are subsequently pressed against the dental tissue, and left in place until the elastomeric material has hardened. This traditional process involves several materials and steps, material waste and fairly lengthy set times.

The invention permits impressioning using a bilayer thermoplastic molding composition. In a preferred embodiment, a flat sheet or a preformed arch-shaped shell is made from two coextruded thermoplastic layers. The physical properties of each layer emulate in part the properties of a conventional rigid shell and the elastomeric impression material respectively. At a suitable elevated temperature the shell layer becomes a conformable, non-sticky melt (thereby permitting the warm shell layer to be hand-shaped into a custom shell configuration) and the elastomer layer exhibits good flow and low viscosity (thereby permitting the warm elastomer layer to flow around tooth structure and provide an accurate model). The warm bilayer construction provides easy placement, accurate impressioning, and efficient use of materials. Cooling can take place rapidly, and in less time than is required to harden a conventional impression. Once cooled, the shell layer exhibits sufficient rigidity to discourage distortion of the impression during removal from the mouth or during subsequent handling. The elastomer layer provides stable, accurate modeling of hard and soft dental tissue. If either the shell or the elastomer layer is crosslinked after the desired custom shape has been attained, then the shape memory properties of the crosslinked layer discourage creep and distortion. In addition, if the elastomer layer is crosslinked, then the shape memory properties of the elastomer layer will aid in making accurate casts using heated gypsum stone substitutes such as hot-melt thermoplastics. The completed impression can be shipped through the mail and exposed to elevated temperatures with reduced risk that the impression will melt or otherwise become permanently distorted.

The thermoplastic impression material is a heat-softenable substance that is a solid at 38° C. Preferably it is free of objectionable taste or odor, and safe for use in the mouth. Selection of the thermoplastic impression material should be based in part on the desired tray configuration and the desired properties of the impression material in the molten or softened ("warm impression") and solid ("cool impression") states. The warm impression state is characterized by appreciable mass flow of the thermoplastic impression material under moderate (hand) pressure at some temperature between body temperature (about 38° C.) and the maximum temperature that comfortably can be withstood by oral tissues. This maximum temperature is generally thought to be about 75° C., although a maximum of about 65° C. is preferred. The thermoplastic impression material should have sufficient warm impression fluidity to conform accurately to adult dentition and the gingival margin. When evaluated using American Dental Association (ADA) Specification No. 19 for elastomeric dental impression materials using modified test methods described in more detail below, the thermoplastic impression material preferably has a modified consistency disk test value that is greater than about 21. More preferably, the modified consistency disk test value is between about 21 and about 40. Most preferably, it is about 23 to about 30. The cool impression state is characterized by sufficient strength and flexibility after the thermoplastic impression material is resolidified in the mouth to permit removal of the tray from the teeth without tearing or undesirable distortion. This latter requirement is reasonably stringent, and rules out many thermoplastic materials heretofore used in dentistry (e.g., for custom tray manufacture). The preferred thermoplastic impression materials include ethylene vinyl acetate ("EVA") elastomers and thermoplastic segmented polyester elastomers. Suitable EVA elastomers are described in European Published Pat. Appl. No. 0 359 135 and Kokai No. Sho 63[1988]-96536. Preferred commercially available EVA elastomers include the "ELVAX" resins shown below:

| ELVAX Resin | Melt flow rate | % Vinyl acetate |
| --- | --- | --- |
| 40-W | 48–66 | 40 |
| 150 | 38–48 | 33 |
| 220 | 134–168 | 28 |
| 250 | 22–28 | 28 |
| 260 | 5.3–6.7 | 28 |

These are all commercially available from E. I. dupont de Nemours & Co. "ULTRATHENE" EVA resins from Quantum Chemical Corp. and "ESCORENE" EVA resins from Exxon Chemical Co. are also useful.

Suitable segmented polyesters are described in U.S. Pat. Nos. 4,059,715 and 4,552,906.

The elastomer optionally can contain property-modifying or crosslinkable functional groups (for example hydroxyl, acrylate, methacrylate, epoxy, isocyanato or vinyl groups. Blends of elastomers can be used if desired.

Elastomers plasticized with natural plasticizers (e.g., oils) or synthetic plasticizers (e.g., phthalate esters) are particularly preferred. Castor oil, cottonseed oil, mineral oil, orange oil and peanut oil are useful natural plasticizing oils, with triglyceride-containing vegetable oils such as castor oil, cottonseed oil and peanut oil being most preferred. Preferred commercially available synthetic plasticizers include dioctyl adipate; dioctyl sebacate (e.g., "UNIFLEX DOS", Union Camp); "PANALANE" polyisobutylene (Amoco); "PLASTOLEIN" mixed esters such a s grades 9048, 9058 and 9071 (Henkel Corp.); and "SANTIC IZER" phthalates such as grades 160 and 261 (Monsanto, Inc.). Blends of plasticizers can be used if desired.

If desired, the thermoplastic impression material can include a free-radically polymerizable resin containing at least one ethylenically unsaturated monomer, oligomer, or polymer capable of undergoing addition polymerization and containing two or more polymerizable groups. This permits the resin to be crosslinked after an impression has been taken, thereby increasing the impression material's heat resistance and discouraging creep and heat-induced distortion. This will facilitate shipping the completed impression to a remote location (e.g., a dental laboratory) where the model can be poured. Suitable monomers include di- or polyfunctional acrylates and methacrylates such as glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,3-butanetriol trimethacrylate, 1,6-hexanediol diacrylate, 1,4-cyclohexanediol diacrylate, pentaerythritol triacrylate, pentaerythritol tetraacrylate, pentaerythritol tetramethacrylate, sorbitol hexacrylate, bis[1-(2-acryloxy)]-p-ethoxyphenyldimethylmethane, bis[1-(3-acryloxy-2-hydroxy)]-p-propoxyphenyldimethylmethane, tris-hydroxyethylisocyanurate triacrylate, beta-methacrylaminoethyl methacrylate, and mixtures thereof. Other suitable monomers include unsaturated amides such as methylene bis-acrylamide, methylene bis-methacrylamide, 1,6-hexamethylene bis-acrylamide and diethylenetriamine tris-acrylamide. Suitable oligomeric or polymeric resins include 200 to 500 molecular weight polyalkylene glycols, acrylated or methacrylated oligomers such as those of U.S. Pat. No. 4,642,126, acrylated urethanes such as "SARTOMER" SR-349, 9503, 9504 and 9505 (Sartomer Corp.), "INTEREZ" CMD 8803, 8804 and 8805 (Radcure Specialties, Inc.), and "PHOTOMER" 4127, 4072, 6060, 6110 and 6160 (Henkel Corp.), as well as acrylated polyester oligomers such as "EBERCRYL" 830 (Radcure Specialties, Inc.). Mixtures of free-radically polymerizable monomers, oligomers or polymers can be used if desired.

The free-radically polymerizable resin can if desired be cured using a conventional chemical initiator system, such as a combination of a peroxide and an amine. However, chemical cure initiator systems typically require at least partial ingredient separation before use. The resin is preferably cured using a photoinitiator, optionally combined with a suitable photosensitizer or accelerator. The photoinitiator should be capable of generating free radicals for addition polymerization at some wavelength between 200 and 800 nm. Suitable photoinitiators include alpha-diketones, monoketals of alpha-diketones or ketoaldehydes, acyloins and their corresponding ethers, chromophore-substituted halomethyl-s-triazines, chromophore-substituted halomethyl-oxadiazoles, aryliodonium salts, and other commercially available ultraviolet ("UV") and visible light photoinitiators. Preferred photoinitiator systems include a mono or diketone photoinitiator together with a suitable donor compound or accelerator, such as the systems described in U.S. Pat. Nos. 3,427,161, 3,756,827, 3,759,807, 4,071,424, 4,828,583, U.K. Pat. Specification No. 1,304,112, European Published Pat. Appl. No. 150,952 and Chem. Abs. 95:225704U.

A somewhat wider variety of thermoplastic materials can be used to make customizable shells for trays of the invention. The shell preferably is free of objectionable taste or odor, and safe for use in the mouth. Selection of a thermoplastic shell material should be based in part on the desired tray configuration and the desired properties of the shell in the molten or softened ("warm shell") and solid ("cool shell") states. The warm shell state is characterized by appreciable mass flow of the thermoplastic shell material under moderate (hand) pressure at some temperature between body temperature (about 38° C.) and the maximum temperature that comfortably can be withstood by oral tissues. Preferably the shell melts or softens at a temperature less than 60° C. The cool shell state is characterized by sufficient shell strength and stiffness to permit an acceptably accurate dental impression to be made in the tray, and by minimal apparent mass flow of the thermoplastic shell material under moderate pressure at temperatures below 38° C.

The warm shell and cool shell properties permit the tray to be heated to a moderate temperature, manually shaped in the mouth while warm to conform to the shape of hard and soft oral tissue, and cooled within the mouth to form a substantially rigid custom impression tray.

Representative thermoplastic shell materials include polyesters and polyurethanes such as those described in U.S. Pat. Nos. 3,382,202, 4,059,715, 4,182,829, 4,327,013, 4,361,538, 4,552,906 and 4,569,342; copolymers such as those described in U.S. Pat. Nos. 4,659,786, 4,740,245 and 4,768,951; and ethylene vinyl acetate copolymers such as those described above. The thermoplastic shell material preferably is a homopolymer or copolymer of epsilon-caprolactone. The polycaprolactone optionally can contain property-modifying or crosslinkable functional groups (for example hydroxyl, acrylate, methacrylate, epoxy, isocyanato or vinyl groups) if desired. Blends of polycaprolactones can also be employed. Preferred commercially available polycapfolactone polymers include "TONE P-700" and "TONE P-767" (40,000 molecular weight) and "TONE P-300" (10,000 molecular weight) polycaprolactone from Union Carbide Corp., and the "CAPA" polycaprolactones "630" (30,000 molecular weight), "640" (40,000 molecular weight), "650" (50,000 molecular weight), and "656" (56,000 molecular weight) from Interox.

The thermoplastic shell material preferably contains at least one ethylenically unsaturated monomer, oligomer, or polymer capable of undergoing addition polymerization, together with a suitable initiator (e.g., a photoinitiator), such as the ethylenically unsaturated materials and initiators described above. They permit the shell to be crosslinked, thereby imparting shape memory to the thermoplastic shell material and increasing its heat resistance.

Both the thermoplastic shell material and the thermoplastic impression material can contain a wide variety of adjuvants depending upon the desired tray properties. Suitable adjuvants include solvents, diluents, plasticizers, pigments, dyes, inorganic or organic reinforcing or extending fillers, thixotropic agents, indicators, inhibitors, stabilizers, UV absorbers, medicaments (e.g., leachable fluorides), biocides and the like. The thermoplastic shell material preferably contains one or more fillers that increase the material's warm state modulus. Preferred fillers have a fibrous, platy or finely-divided particulate form. For fibrous or platy fillers, the filler preferably has an aspect ratio greater than about 3:1, more preferably greater than about 5:1, and most preferably greater than 10:1. For particulate fillers, the particles preferably have an average particle diameter less than about 100 micrometers, more preferably less than about 10 micrometers, and most preferably less than about 1 micrometer. Particularly preferred fillers include glass fibers, clay, mica, alumina, submicron silica (for example, fumed, precipitated or colloidal silica) and finely-divided calcium carbonate. The fillers can be untreated or treated with a suitable coupling agent (for example, a silane).

The types and amounts of ingredients in the thermoplastic impression material and the thermoplastic shell material usually will be empirically selected. Both thermoplastic materials preferably should remain substantially homogeneous (that is, they should not undergo macroscopic phase separation or filler sedimentation). Subject to the effects of any shape memory imprinted in the shell, the tray preferably should retain its desired physical properties even if repeatedly cycled between the warm and cool states. Thus the selection of ingredients can be guided in part by the desire to preserve homogeneity and thermal reversibility.

The preferred amounts of thermoplastic elastomer and plasticizer in the thermoplastic impression material are as follows:

| Ingredient | Preferred Weight % | Most Preferred Weight % |
| --- | --- | --- |
| Thermoplastic elastomer | 30 to 90 | 40 to 60 |
| Plasticizer | 10 to 70 | 20 to 40 |
| Polymerizable resin | 0 to 60 | 20 to 40 |
| Initiator | 0 to 10 | 0 to 5 |

The preferred amounts of thermoplastic, polymerizable resin, initiator and filler in the thermoplastic shell material are as follows:

| Ingredient | Preferred Weight % | Most Preferred Weight % |
| --- | --- | --- |
| Thermoplastic | up to 90 | 80 to 40 |
| Polymerizable resin | 0 to 50 | 0 to 35 |
| Initiator | 0 to 10 | 0 to 5 |
| Filler | 0 to 70 | 20 to 60 |

The ingredients can be blended by hand or by mechanical mixing. The ingredients preferably are warmed sufficiently to melt the thermoplastic portion, but if desired can be mixed at lower temperatures. Any suitable mixing device can be used, including kettles equipped with a mechanical stirrer, extruders, rubber mills, and the like.

As noted above, the tray can also have a rigid shell. A wide variety of rigid shell materials can be used. Preferably the chosen material is free of objectionable taste or odor, and safe for use in the mouth. Suitable materials include metals (e.g., stainless steel) and rigid plastics (e.g., polystyrene, polypropylene, or polyamide). Injection-moldable plastics are preferred. If desired, fillers or stiffening ribs can be used to increase the shell's rigidity.

Particularly preferred trays with rigid shells can be prepared from currently-available stock trays available from dental suppliers. These can be preloaded by partially filling the shell with the above-described thermoplastic impression materials, and then packaging the tray for shipment. Suitable shells include disposable trays such as the "TRIPLE TRAY" double bite tray (Espe-Premier), the "OCCLUSAL HARMONY" closed bite impression tray, the "COE" spacer tray (Coe, Inc.), the "MASTER TRAY" full arch tray (Teledyne Getz), and the "FUZZY TRAY" full arch tray (Laclede Inc.).

The tray preferably includes an adhesion-promoting scrim between the tray and the thermoplastic impression material. A variety of woven, nonwoven or perforated sheetlike materials can be used to form the scrim. Suitable woven materials include cloth or gauze formed of natural or synthetic fibers such as cotton, polyester (e.g., "DACRON" fibers, and "SONTARA" fabrics such as polyester grades 8000, 8027 and 8100, E. I. dupont de Nemours & Co.), polyethylene, polypropylene, polyurethane, polyamide (e.g., "NYLON" fiber), polyaramide (e.g., "KEVLAR" fiber) and glass (e.g., "FIBERGLAS" fiber). The scrim can be a conventional weave or a nonconventional weave such as either of the "hook" or "loop" fabrics used in hook and loop fasteners. Suitable nonwoven materials include felt and randomly-laid polyester (e.g., "BONAR" fabrics such as "ULTRALOFT" powder-bonded polyester grades 60B-9125, 60B-9628 and 60B-9928, Bonar Fabrics Corporation). Suitable perforated sheetlike materials include fine pitch polypropylene net. The scrim preferably should bond well to both the shell and to the thermoplastic impression material, be free of objectionable taste or odor, and be safe for use in the mouth. The scrim also preferably has a melting temperature above the melting or softening temperature of the thermoplastic impression material. Woven or perforated sheetlike scrim materials preferably have a mesh size and surface topography sufficient to provide the desired degree of adhesion between the shell and the impression material.

If desired, the scrim can be treated with an appropriate primer or coupling agent to aid adhesion to the shell or to the thermoplastic impression material. If visible through the preloaded thermoplastic impression material, the scrim can be printed with instructions for the user or imprinted with a suitable trademark.

Preferably one or more spacers are fastened either atop or beneath the scrim. These aid in controlling the amount of impression material that will be loaded into the tray, and in preventing unduly thin impressions which may perforate or tear upon removal from the mouth. Preferably at least one of the spacers is thermoplastic. By heating a thermoplastic spacer or the scrim prior to assembly, a firm bond between spacer and scrim will readily be achieved.

For trays having either a thermoplastic or a rigid shell, sufficient thermoplastic impression material should be preloaded into the shell to provide accurate envelopment of typical adult dentition and the gingival margin when the impression is made. Typically, about 15 to 30 ml of thermoplastic impression material will be needed for a full arch tray. Owing in part to the relatively low cost of the thermoplastic impression material, larger quantities (e.g., 30 to 50 ml) can be used if desired. Lesser quantities can of course be used for small trays (e.g., partial arch trays). Larger quantities may of course be needed for double bite trays than for single bite trays. Preferably, empirical in vivo trials will be used to establish the preferred thermoplastic impression material quantity for a given tray configuration or shape.

The thermoplastic impression material is conveniently preloaded in the shell by heating the impression material until it becomes a free-flowing liquid, pouring it into the shell, and then cooling the resulting tray for shipment or storage. A level fill is preferred for reasons of manufacturing convenience, although non-level filling (e.g., by tipping the shell from side to side during preloading to coat the inside of the shell, or by using a rounded coating head whose shape conforms generally to the inside of the shell) can be employed if desired.

The tray can be packaged using any convenient packaging materials, including paper or plastic bags, pouches or boxes. If desired, a peel-off cover can be adhered to the top of the tray to prevent loss or spillage of the thermoplastic impression material if the tray is inadvertently heated during shipment or storage.

When ready for use, the tray is heated using any convenient means until the preloaded thermoplastic impression material melts or softens. The tray can be immersed in a heated bath containing a suitable inert liquid (for example, water or a fluorochemical fluid) that will not dissolve or swell the tray in either its cool or warm states. The tray can also be softened using heat sources such as a hot air gun, hot plate, conventional oven, infrared heater or microwave oven. The tray can be encased in a plastic pouch or other container which is in turn heated (e.g., electrically), or subjected to one or more of the above-mentioned heating methods. For meltable thermoplastic impression materials, the increase in transparency that typically occurs at the melting point will provide a convenient indicator of sufficient heating. The warmed tray should be promptly inserted in the patient's mouth, (and, if made using a heat-softenable thermoplastic shell, shaped to conform to the patient's dentition), and permitted to cool until the impression material resolidifies.

Transforming the tray from a warm impression state to a cool impression state requires loss of thermal energy and can be carried out using a variety of cooling techniques. Cooling can take place under ambient conditions in the presence of air only. Cooling can be expedited using forced air, cold water, ice, or heat sinks such as chilled "cold packs" or flexible pouches containing low boiling inert liquids. Of particular interest for dental applications are chilled cold packs in flexible pouches that have been preshaped to match the contours of the tray. For example, flexible pouches containing a chilled coolant can be fabricated in the shape of a full arch or quadrant and placed intraorally in contact with the warm tray.

Shape memory can be imparted to trays of the invention whose shells contain thermoplastic impression material, free-radically polymerizable resin and initiator. The resin is allowed or caused to harden (for example, by exposing shells containing a photoinitiator to a suitable light source). Polymerization can take place before or after the warmed, softened shell is allowed to cool, although carrying out polymerization after cooling will tend to lengthen polymerization times. After polymerization, the shell preferably retains sufficient elasticity to permit ready removal of the model. The polymerized, cooled shell will exhibit shape memory. Accordingly, it will be more resistant to heat and handling stresses than shells made solely from a thermoplastic. If the shell is accidentally distorted, it can be returned to its custom shape by reheating it to its warm shell state while in a relaxed condition. For example, the tray can be immersed in a hot water bath and removed for cooling after the custom shape has reappeared. While still in the warm shell state, it will remain pliable, and accordingly will exhibit semi-thermoplasticity. This permits the custom shape to be adjusted if desired.

The following examples are offered to aid in understanding the invention and are not to be construed as limiting its scope. Unless otherwise indicated, all parts and percentages are by weight.

EXAMPLE 1

A filled thermoplastic custom shell composition was prepared by combining 22.5 parts "TONE P-767" 40,000 molecular weight polycaprolactone (Union Carbide Corp.), 7.5 parts "SR-9505" urethane diacrylate oligomer (Sartomer Corp.), 1.2 parts "EBERCRYL 830" polyester hexacrylate (Radcure Specialties, Inc.), 45 parts "VICRON" calcium carbonate (Pfizer Corp.), 10 parts "SIPERNAT D-11" treated precipitated silica (North American Silica Co.), 5 parts "ULTRASIL VN 3 SP" untreated precipitated silica (North American Silica Co.), 4 parts "1156" chopped glass fibers (PPG), and 0.75 parts each camphorquinone ("CPQ") and p-ethyldimethylaminobenzoate ("EDMAB"). The ingredients were stirred in a warm vessel at about 100° C. until homogeneous. The resulting mixture was cast atop polyester film into a 2.5 mm thick layer into which was pressed a web of "SONTARA 8000" nonwoven material (E. I. DuPont de Nemours & Co.). The warm assembly was cut into generally U-shaped pieces using a "cookie cutter" style cutting implement. Each piece was squeezed while still warm between two halves of a silicone mold to form an arch-shaped, nonwoven scrim-lined customizable shell.

A thermoplastic impression material was prepared by melt blending 20 parts each "ELVAX 150" and "ELVAX 40" EVA resins (E. I. dupont de Nemours & Co.), 25 parts cottonseed oil, and 0.01 parts "ULTRAMARINE BLUE A 9829" (Kohnstamm Co.). The oil was heated first to about 120° C. in a mechanical stirring device. The resin was added in small portions with stirring, followed by the dye. The molten mixture was poured into the customizable shell and allowed to cool. The cooled thermoplastic impression material had a rubbery consistency.

The resulting tray could be easily softened by immersing the tray in a 60° C. water bath for about three minutes. By pressing the tray against the upper arch of a human volunteer, asking the volunteer to bite down on the softened impression material, hand-shaping the shell to conform to the volunteer's dentition, permitting the tray to cool, and then removing the tray, an accurate replica of the volunteer's upper arch and gingival margin is obtained. Tray removal is fairly easy and is accomplished without tearing or delamination of the resolidified impression material.

By irradiating the tray for two minutes in a "STAR-CURE" curing chamber (Star X-ray, Inc.), a tray with shape memory is obtained. The tray can also be photocured by setting it under a conventional dental operatory light (for example, a "RITTER STAR LIGHT", Sybron Corp.) for about two minutes per side.

Very satisfactory dental models are obtained by pouring a conventional gypsum stone slurry into the completed impression and allowing the gypsum to harden. Removal of the model is easy, and is accomplished without breakage of the hardened gypsum.

EXAMPLE 2

A thermoplastic tray material was prepared by combining 39.7 parts "TONE P-767" polycaprolactone, 11.8 parts "SR-9505" urethane diacrylate oligomer, 2 parts "EBERCRYL 830" polyester hexacrylate, 20 parts "3075" chopped glass fibers (PPG), 11.7 parts "QUSO WR55" hydrophobic silica (North American Silica Co.), 16.6 parts "ULTRASIL VN 3 SP" untreated precipitated silica, 0.9 parts EDMAB, and 0.23 parts CPQ. The ingredients were blended and molded into a shell using the method of EXAMPLE 1. The interior of the completed shell was softened by heating it under an infrared lamp. A sheet of "SONTARA 8027" polyester fabric (E. I. dupont de Nemours & Co.) was pressed into the heated shell surface, and the shell was allowed to cool.

One quadrant of the the shell was preloaded with the molten thermoplastic impression material of EXAMPLE 1. After cooling, the resulting tray was rewarmed in a 60° C. water bath, removed and shaken to remove excess water. "IMPRINT" vinyl polysiloxane single phase impression material was syringed into the other quadrant of the shell. The resulting tray was then placed in Dr. Oxman's mouth, shaped to conform to his upper arch, and allowed to cool until both impression materials had hardened. A gypsum stone model was poured in the completed impression. Both quadrants of the model exhibited good detail reproduction, with no apparent difference in quality between the two quadrants.

EXAMPLE 3

The "OCCLUSAL HARMONY" closed bite tray includes a bite wafer believed to be made of polycaprolactone. If warmed before insertion in the mouth, the bite wafer can be used to record occlusal registration. The bite wafer is only about 3 mm thick, and in solid form it is relatively inflexible. Thus it could not be used to make full-depth impressions of adult teeth. Instead, the user typically must fill the tray with a conventional two-part impression material such as an addition-cure silicone or a polyether.

The "OCCLUSAL HARMONY" tray was filled to the top of its sidewalls with the molten thermoplastic impression material of EXAMPLE 1. After cooling, the resulting preloaded stock tray was used to make a closed bite partial arch impression. The tray was heated in a 70° C. water bath for about 3 minutes, until both the thermoplastic impression material and the bite wafer had softened. The tray was placed into the mouth of a human subject and cooled to form an impression as in EXAMPLE 1. The occlusal detail appeared to be more faithfully reproduced than the detail obtained from a corresponding impression made by filling the tray with a conventional polysiloxane impression material.

EXAMPLE 4

The procedure of EXAMPLE 3 was repeated using a "TRIPLE TRAY" double bite impression tray (Espe-Premier). The resulting preloaded stock tray yielded impressions with excellent detail reproduction.

EXAMPLE 5

The procedure of EXAMPLE 3 was repeated using a "MASTER TRAY" full arch plastic tray (Teledyne Getz, Inc.). The resulting preloaded stock tray yielded impressions with excellent detail reproduction.

EXAMPLE 6

An aliphatic segmented thermoplastic polyester was prepared by measuring out the ingredients set out below in TABLE I:

TABLE I

| Ingredient | Parts |
| --- | --- |
| Poly(tetramethylene ether) diol[1] | 49.53 |
| Adipic acid | 29.21 |
| 1,6-hexanediol | 21.26 |
| Antioxidant[2] | 0.10 |
| Antimony oxide | 0.10 |

[1]"POLYMEG 2000" (Quaker Oats Chemical).
[2]"IRGANOX 1010" (Ciba Geigy Corp.).

The "POLYMEG 2000" diol and 1,6-hexanediol were transferred to a three neck flask fitted with a mechanical stirrer, condenser, "Dean-Stark" trap, heating mantle, thermometer and nitrogen inlet. The diols were stirred at moderate speed under a nitrogen purge for 5–10 minutes while heating to a temperature of 100° C. Adipic acid was slowly added and the mixture heated to a temperature of about 140°–150° C. Water began collecting in the trap. The reaction was continued until at least 80% complete on the basis of water volume collected. The reaction mixture was cooled to 150° C. and the trap removed. The antioxidant and antimony oxide were then added to the flask. The flask was purged with nitrogen for 5 minutes. Following the purge, the flask was attached to a vacuum line and the pressure reduced while maintaining a reaction temperature of 150° C.

After 30 to 60 minutes a vacuum of <0.1 mm Hg was attained and the reaction temperature increased to 230° C. The reaction was continued until the acid number had decreased to less than 1 mg KOH/gm sample. The resulting semi-crystalline thermoplastic composition contained about 53% amorphous segment content and exhibited rubbery, elastomeric properties in the solid state.

A blend of this segmented polyester and a free-radically polymerizable acrylate resin ("CMD-880", Interez) was prepared by transferring the ingredients set out below in TABLE II to a glass vessel heated to 80° C.:

TABLE II

| Ingredient | Parts |
| --- | --- |
| Segmented polyester | 80.0 |
| Urethane acrylate | 20.0 |
| CPQ | 0.25 |
| EDMAB | 0.50 |

The ingredients were heated until molten and mixed thoroughly with a spatula until homogeneous. The resultant blend was cast into a sheet and cooled, yielding a thermoplastic elastomer.

The neat segmented polyester and the segmented polyester/acrylate blend were evaluated by measuring warm impression state viscosity at 65° C. using a rheometric dynamic analyzer (Rheometrics, Inc.) operated at 20% maximum strain and 1 radian/second strain rate.

Cool impression state storage modulus was measured at 30° C. on the rheometric dynamic analyzer, operated at 1.4% maximum strain and a 10 radian/second strain rate, on samples that were 1) not irradiated ("NIR") or 2) irradiated under "hot" conditions ("IR HOT") while the sample was at about 50°–55° C., using a "VISILUX 2" dental curing lamp (3M).

Dimensional stability was evaluated using a modified version of ADA Test Specification No. 19. Each composition was heated to 80° C. until molten and poured onto the ruled die prescribed in the Test Specification. A transparent rigid plate was placed atop the molten composition, and secured to the ruled die with a clamp. The molten composition was allowed to cool for 5 minutes at room temperature. The clamp and solidified molding composition were removed from the die. The resulting solid sample was stored at 23°±1° C. and 50±5% relative humidity for 24 hours. Dimensional stability was determined by comparing the distances between the ruled lines on the sample and on the ruled die using an optical comparator.

Compression set was evaluated using a modified version of ADA Test Specification No. 19. Each composition was heated to 80° C. until molten and transferred to the standard compression set cylindrical mold prescribed in the Test Specification. The mold endplates were clamped into place and the mold and its contents cooled in a 22° C. water bath for 5 minutes. The resulting solid sample was removed from the mold. Each sample was axially compressed 1.0 mm for 30 seconds using a metered screw clamp. The clamp was released and a measurement of permanent deformation recorded one minute later. The percentage change in cylinder height was calculated to determine compression set.

Strain-in-compression was evaluated using a modified version of ADA Test Specification No. 19. Cylindrical samples were prepared according to the compression set test described above. The cylinder height was measured, a 1.125 kg mass was placed atop tile cylinder, and a second height measurement was recorded thirty seconds later. The percentage change in cylinder height was calculated to determine strain-in-compression.

The results for each composition are set out below in TABLE III:

TABLE III

| Run no. | Polyester/ acrylate ratio | Viscosity, 65° C., kilopoise | Modulus, 30° C., dyne/cm$^2$ × 10$^8$ | | Dimensional stability % shrinkage | | Compression set, % | strain-in-compression, % |
| --- | --- | --- | --- | --- | --- | --- | --- | --- |
| | | | NIR[1] | IR Hot[2] | NIR | IR Hot | | |
| 1 | 100/0 | 2.7 | 0.5 | NM[3] | 0.25 | NM | 0.96 | 0.63 |
| 2 | 80/20 | 2.2 | 0.6 | 0.8 | 0.23 | 0.12 | 0.84 | 1.78 |

[1]"NIR" = Not irradiated.
[2]"IR Hot" = Irradiated hot.
[3]"NM" = Not measured.

EXAMPLE 7

In a series of runs, thermoplastic impression materials were prepared from a variety of plasticized elastomers. The elastomers were blended as described in EXAMPLE 1.

Consistency was evaluated using a modified version of ADA Test Specification No. 19. Each composition was heated in an oven at 80° C. until molten, then transferred to the standard polyethylene-covered plate described in the Test Specification. Thirty seconds after removal of the composition from the oven, the sample was covered with a second polyethylene sheet, a 75 g glass plate and a 500 g weight. Seven minutes later the major and minor diameters of the resulting thin disk were measured and averaged. Because the values obtained were very reproducible from sample to sample, only one or two samples of each composition were evaluated rather than the three samples specified in the original Test Specification.

Set out below in TABLE IV are the ingredients in each impression material, and the measured modified consistency disk test values.

TABLE IV

| Run No. | EVA Resin | | Plasticizer | | Polymerizable Resin | | Modified Consistency Disk Test |
| --- | --- | --- | --- | --- | --- | --- | --- |
| | Type | Parts | Types | Parts | Type | Parts | |
| | ELVAX 150 | .228 | Cottonseed oil | .478 | | | 26.5 |
| | ELVAX 250 | .2 | Limonene | .143 | | | |
| 2 | ELVAX 140 | 20 | Cottonseed oil | 25 | | | 23 |
| | ELVAX 150 | 20 | | | | | |
| 3 | ELVAX 220 | 1 | Peanut oil | 1 | | | 27 |

TABLE IV-continued

| Run No. | EVA Resin Type | Parts | Plasticizer Types | Parts | Polymerizable Resin Type | Parts | Modified Consistency Disk Test |
|---|---|---|---|---|---|---|---|
| 4 | ELVAX 220 | 4 | Peanut oil | 6 | | | 30.5 |
| 5 | ELVAX 150 | 2 | Peanut oil | 3 | | | 29 |
| 6 | ELVAX 150 | 1 | Peanut oil | 3 | | | 28 |
|   | ELVAX 240 | 1 | | | | | |
| 7 | ELVAX 40W | 3 | Peanut oil | 2 | PHOTOMER 4127 | 2 | 26 |
|   | ELVAX 210 | 2 | | | | | |
| 8 | ELVAX 40W | 3 | Peanut oil | 4 | PHOTOMER 4127 | 1 | 27 |
|   | ELVAX 210 | 2 | | | | | |
| 9 | ELVAX 40W | 3 | Peanut oil | 3 | PHOTOMER 4127 | 2 | 26.5 |
|   | ELVAX 210 | 2 | | | | | |
| 10 | ELVAX 40W | 7.5 | Peanut oil | 5 | PHOTOMER 4127 | 25 | 27.5 |
|    | ELVAX 150 | 12.5 | | | | | |
| 11 | ELVAX 40W | 7.3 | Peanut oil | 13 | PHOTOMER 4127 | 17.5 | 28.5 |
|    | ELVAX 150 | 12.2 | | | | | |

1. "ELVAX" resins are commercially available from E. I. duPont de Nemours Co.
2. "PHOTOMER" resins are commercially available from Henkel Corp.

Although this invention has been described using certain illustrative examples, it should be understood that the invention is not limited to the specific exemplary embodiments shown in this specification.

We claim:

1. A method for preparing a dental model using a preloaded impression tray, comprising the steps of:
   (a) heating a thermoplastic impression material in the tray until the material melts or softens, the material being a solid at 38° C. and having:
      (i) a softening point that comfortably can be withstood by oral tissues,
      (ii) sufficient depth in the tray and fluidity when softened to conform accurately to adult dentition and the gingival margin, and
      (iii) sufficient flexibility when resolidified in the mouth to permit removal of the impression material from teeth without tearing or undesirable distortion; and, after a dental impression has been taken using the tray;
   (b) pouring a modeling compound into the impression to form a dental model.

2. A method according to claim 1, wherein the impression material comprises an ethylene vinyl acetate copolymer or a segmented polyester.

3. A method according to claim 2, wherein the impression material contains a natural or synthetic plasticizer.

4. A method according to claim 3, wherein the plasticizer comprises cottonseed oil, peanut oil, an adipate ester, or a sebacate ester.

5. A method according to claim 2, wherein at least one of the tray and the impression material comprises a polymerizable resin.

6. A method according to claim 5, further comprising the step of polymerizing the resin after the impression has been taken.

7. A method according to claim 1, wherein the tray has a heat-softenable thermoplastic shell that melts or softens at a temperature less than 60° C.

8. A method according to claim 1, wherein the tray has a rigid metal or plastic shell.

9. A method according to claim 1, wherein the tray has been packaged in a paper or plastic bag, pouch or box before the heating step.

10. A preloaded impression tray comprising a thermoplastic impression material at least partially enveloped by a shell, the thermoplastic impression material being a plasticized solid and having:
    (i) a softening point that comfortably can be withstood by oral tissues,
    (ii) sufficient depth in the shell and fluidity when softened to conform accurately to adult dentition and the gingival margin, and
    (iii) sufficient strength and flexibility when resolidified in the mouth to permit removal of the impression material from teeth without tearing or undesirable distortion, wherein the impression material has a modified consistency disk value greater than 21.

11. A preloaded impression tray according to claim 10, wherein the modified consistency disk value is between 21 and 40.

12. A preloaded impression tray according to claim 10, wherein the modified consistency disk value is between 23 and 30.

13. A preloaded impression tray comprising a thermoplastic impression material at least partially enveloped by a shell, the thermoplastic impression material being a plasticized solid and having:
    (i) a softening point that comfortably can be withstood by oral tissues,
    (ii) sufficient depth in the shell and fluidity when softened to conform accurately to adult dentition and the gingival margin, and
    (iii) sufficient strength and flexibility when resolidified in the mouth to permit removal of the impression material from teeth without tearing or undesirable distortion, wherein the impression material comprises an ethylene vinyl acetate copolymer or segmented polyester, together with a natural or synthetic plasticizer, further comprising a polymerizable resin and a photoinitiator.

* * * * *